NEW AND DISTINCT VARIETY OF BLUEGRASS PLANT

Filed Sept. 17, 1970

United States Patent Office

Plant Pat. 3,151
Patented May 2, 1972

3,151
NEW AND DISTINCT VARIETY OF BLUEGRASS PLANT

Cyril Reed Funk, Jr., Milltown, N.J., assignor to Rutgers University, New Brunswick, N.J.

Filed Sept. 17, 1970, Ser. No. 73,271
Int. Cl. A01h 5/00
U.S. Cl. Plt.—88 1 Claim

ABSTRACT OF THE DISCLOSURE

A Kentucky bluegrass plant which exhibits a rich, dark green color, a moderately fine leaf texture, good rhizome and tiller development, a short ligule without hair, and moderately small panicles and spikelets, with three florets per spikelet. The plant has very good turf density and horizontal spreading ability and is highly resistant to common grass diseases, particularly stripe smut, powdery mildew, and leaf rust.

The present invention relates to a new and distinct variety of Kentucky bluegrass plant, and more particularly to a bluegrass plant which exhibits an attractive dark green color and excellent resistance to stripe smut disease.

The new variety was discovered by me in a cultivated lawn in Albany, N.Y. An attractive, vigorous, dark green, fine textured patch of grass was observed in an area where most other bluegrass plants were doing poorly or had been replaced by crabgrass and other unwanted weeds. Plant material from this spot was taken to a greenhouse, and I asexually reproduced additional plants of the variety by the method of vegetative propagation. After growth in the greenhouse, the vegetatively reproduced plants were transferred to field nurseries for increase and subsequent turf evaluation. Progeny tests were conducted and showed that the plant could also be reproduced asexually by means of disseminules. The plant was identified as "NJE P–29" bluegrass.

NJE P–29 bluegrass exhibits a unique combination of characteristics which distinguishes it from all other varieties of which I am aware. Of special moment is its attractive dark green color which is maintained throughout most of the growing season, in combination with excellent resistance to stripe smut disease incited by the fungus *Ustilago striiformis*. The new variety exhibits good to excellent resistance to powdery mildew disease caused by the fungus *Erysiphe graminis* and to leaf rust disease caused by the fungus *Puccinia poae-nemoralis*. The variety is highly apomictic and has a leafy turf-type growth habit tolerant of moderately close mowing.

A primary object of the invention is to provide a new and distinct bluegrass plant having the desirable characteristics referred to above and to be described in detail below.

Other objects and advantages of the invention will become more fully apparent from the following detailed description when taken in conjunction with the accompanying illustrations, in which.

Figure 1:
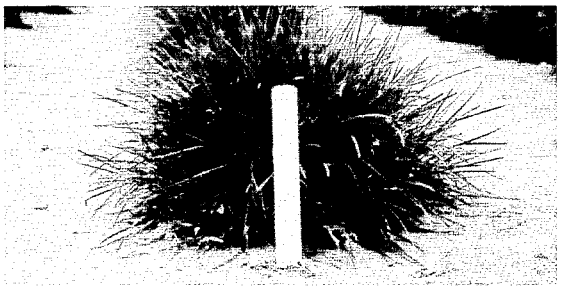
FIG. 1 shows a plant of the new variety approximately one week before the flowering stage.
Figure 2:
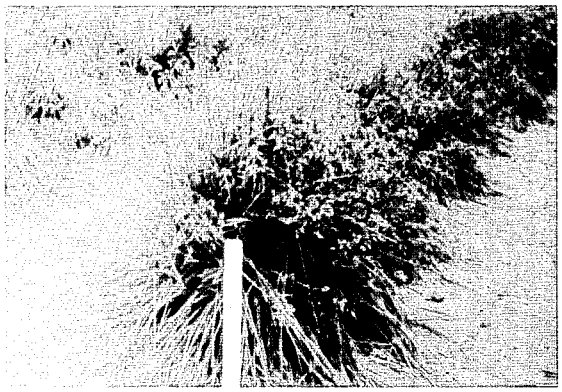
FIG. 2 shows a plant of the new variety under different lighting conditions after the completion of the flowering stage.
Figure 3:
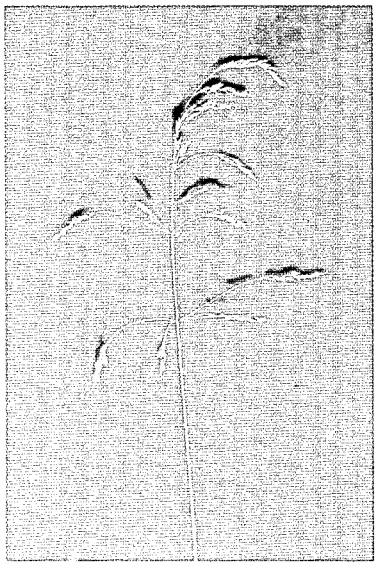
FIG. 3 shows a panicle of the new variety about four weeks after the completion of the flowering stage.

NJE P–29 Kentucky bluegrass (*Poa pratensis*) is perennial with creeping rhizomes forming a dense, moderately compact turf. The variety possesses the following unique combination of characteristics.

(1) Excellent resistance to stripe smut disease;
(2) Excellent resistance to powdery mildew disease;
(3) Very good resistance to leaf rust disease;
(4) A leafy turf-type growth habit tolerant of moderately close mowing;
(5) Moderately good resistance to leaf spot and crown rot disease;
(6) An attractive, rich, dark green color which is maintained throughout most of the growing season;
(7) Very good rhizome and tiller development, producing a turf of excellent density, very good horizontal spreading ability, high performance and excellent persistence;
(8) Moderately fine leaf texture;
(9) Moderately small panicles and spikelets; and
(10) A short ligule without hair.

PLANT DESCRIPTION

The culms of NJE P–29 are moderately erect but are generally bent at the lower nodes. The culms are tufted, moderately slender, cylindrical, smooth and glossy, usually have 4 to 5 nodes, and average 64 cm. in height when undisturbed by mowing. The leaves are dark green; sheaths smooth and hairless with those on the vegetative shoots compressed and keeled; ligules membraneous, without hair and very short on vegetative tillers but about 0.6 to 0.9 mm. long on reproductive tillers; edge of collar fringed with fine hairs; blades 3 to 4 mm. wide, initially folded but subsequently opening out with a boat-shaped tip. Panicles pyramidal, open, with main axis fairly erect and averaging 88 mm. long; lower branches mostly in clusters of 3 to 5 (average 3.9). Spikelets ovate, compressed, usually 4 to 5 mm. long (average 4.5 mm.), three-flowered, breaking up at maturity beneath each lemma. Glumes persistent, unequal, rough on the keels; lower ovate 2.1 to 2.8 mm. long (average 2.5 mm.), 1–3 nerved; upper ovate to elliptic, 2.6 to 3.2 mm. long (average 2.9 mm.), 3-nerved. Lemmas five-nerved, overlapping oblong or ovate-oblong in side view averaging 2.96 mm. long, blunt and slightly pointed, having a purplish tinge near the edges, fine hairs on the keel and marginal nerves of the lower half of the lemma with longer fine crinkled hairs at the base. Paleas nearly as long as the lemmas with two keels. Caryopsis tightly enclosed by the lemma and palea.

Since environmental factors such as day length, temperature, soil fertility and moisture influence morphological characteristics to some degree, these characteristics may vary slightly under different conditions. The morphological characteristics of NJE P–29 and other bluegrasses measured in 1970 at Adelphia, N.J., are shown in Table 1.

TABLE 1.—MORPHOLOGICAL COMPARISON OF NJE P-29 AND OTHER BLUEGRASS VARIETIES

| Variety | Plant height, cm. | Plant diameter, cm. | Leaf blade width, mm. | Hairs on edge of collar [1] | Hairs on ligule [1] | Flag leaf length, mm. | No of panicles per plant | Panicle color [2] | Panicle erect or nodding [3] | Number of branches at lowest panicle node | Panicle length, mm. |
|---|---|---|---|---|---|---|---|---|---|---|---|
| NJE P-29 | 64 | 32 | 3.0 | 2.5 | 0.0 | 55 | 252 | 2.5 | 2.0 | 3.9 | 88 |
| Delta | 73 | 17 | 2.6 | 1.5 | 0.0 | 67 | 196 | 2.0 | 1.0 | 4.8 | 100 |
| Geary | 80 | 24 | 2.9 | 2.0 | 0.0 | 80 | 177 | 3.0 | 3.0 | 4.0 | 134 |
| Newport | 79 | 30 | 4.8 | 3.7 | 3.7 | 77 | 246 | 2.5 | 2.0 | 4.3 | 105 |
| Palouse | 79 | 24 | 3.0 | 1.0 | 0.0 | 93 | 151 | 3.0 | 3.5 | 4.4 | 92 |
| Anheuser Dwarf | 67 | 30 | 5.1 | 2.5 | 2.0 | 51 | 109 | 3.0 | 2.5 | 3.4 | 96 |
| Belturf | 70 | 35 | 3.0 | 2.0 | 1.0 | 58 | 201 | 2.0 | 2.0 | 4.0 | 104 |
| Flyking (Patent 2,887) | 60 | 34 | 4.0 | 1.5 | 1.5 | 68 | 164 | 3.5 | 5.0 | 4.9 | 118 |
| Merion | 70 | 24 | 4.3 | 3.5 | 0.5 | 69 | 280 | 2.0 | 1.5 | 3.5 | 102 |
| Pennstar | 59 | 34 | 3.7 | 2.2 | 1.0 | 66 | 132 | 3.5 | 4.0 | 4.5 | 106 |

[1] Scale: 0=no hairs; 5=most hairs.
[2] Scale: 0=green; 5= purple.
[3] Scale: 1=erect; 5=nodding.

DISEASE RESISTANCE

A comparison of NJE P–29 and other bluegrasses for resistance to stripe smut caused by the fungus *Ustilago striiformis*, powdery mildew caused by the fungus *Erysiphe graminis*, leaf rust caused by the fungus *Puccinia poae-nemoralis*, and leaf spot caused by the fungus *Helminthosporium vagans* is given in the following tables:

TABLE 2.—RELATIVE COMPARISON OF STRIPE SMUT DISEASE RESISTANCE FOR NJE P–29 AND OTHER BLUEGRASSES AT NEW BRUNSWICK, N.J.

| Variety | Stripe smut reaction (1964) [1] | Stripe smut infected tillers per sq. ft. (1965) | (1966) |
|---|---|---|---|
| NJE P-29 | 1 | 0 | 0 |
| Merion | 8 | 148 | 230 |
| Windsor (Patent 2,364) | 6 | 40 | 110 |
| Delta | 3 | 9 | 2 |
| Anheuser Dwarf | | 0 | 1 |
| Fylking | | 0 | 3 |
| Pennstar | | 0 | 2 |
| Belturf | | 0 | 5 |

[1] Scale: 1=most resistant; 8=least resistant.

TABLE 3

Relative comparison of powdery mildew disease resistance for NJE P–29 and other bluegrasses under greenhouse conditions at new Brunswick, N.J.

| Variety: | Mildew rating [1] |
|---|---|
| NJE P–29 | 0.9 |
| Merion | 6.9 |
| Windsor | 2.5 |
| Fylking | 3.9 |
| Pennstar | 4.2 |
| Belturf | 4.3 |
| Newport | 0.8 |
| Sodco | 2.0 |

[1] Scale: 0=no disease; 9=most disease.

TABLE 4

Relative comparison of leaf rust disease resistance for NJE P–29 and other bluegrasses at New Brunswick, N.J. in 1970

| Variety: | Rust disease rating [1] |
|---|---|
| NJE P–29 | 0.6 |
| Merion | 3.5 |
| Delta | 1.5 |
| Anheuser Dwarf | 0.6 |
| Fylking | 1.5 |
| Pennstar | 1.5 |
| Belturf | 1.5 |
| Newport | 3.5 |
| Geary | 3.0 |

[1] Scale: 0=no rust; 9=most diseases.

TABLE 5.—RELATIVE COMPARISON OF LEAF SPOT DISEASE FOR NJE P–29 AND OTHER BLUEGRASSES AT NEW BRUNSWICK, N.J.

| Variety | Percent leaf spot damage (1965) | (1966) | (1968) |
|---|---|---|---|
| NJE P-29 | 12 | 23 | 19 |
| Merion | 5 | 11 | 16 |
| Windsor | 28 | 35 | 45 |
| Delta | 70 | 48 | 33 |
| Anheuser Dwarf | 2 | | 5 |
| Fylking | 6 | | 11 |
| Pennstar | 6 | | 11 |
| Belturf | 20 | | 65 |

The tests summarized in the foregoing tables show that NJE P–29 has excellent resistance to stripe smut, good to excellent resistance to powdery mildew and leaf rust, and moderately good resistance to leaf spot.

REPRODUCTION AND PROPAGATION

Asexual reproduction of NJE P–29 by propagules (tillers and rhizomes) and by disseminules (modified caropses produced by agamospermy) has consistently produced progency plants indistinguishable from the mother plant. The new variety is highly aggressive, as illustrated by Table 6:

TABLE 6.—AGGRESSIVENESS OF VARIOUS BLUEGRASS VARIETIES AS MEASURED BY THEIR ABILITY TO SPREAD UNDER CONDITIONS OF CLOSE MOWING AND COMPETITION FROM OTHER BLUGRASSES.

| Variety | Amount of incroachment into adjacent bluegrass varieties "inches" (1965) | (1966) |
|---|---|---|
| NJE P-29 | +18.0 | +10.5 |
| Pennstar | +2.5 | +4.0 |
| Fylking | +2.5 | +3.0 |
| Anheuser Dwarf | +2.0 | +3.0 |
| Merion | −1.5 | −2.0 |
| Windsor | −1.5 | −5.0 |
| Delta | −3.0 | |
| Kenblue | | −4.0 |
| Park | | −4.0 |
| Fjord | | −5.0 |
| Delta | | −5.0 |

In addition to its attractive dark green color and good disease resistance, the new variety has demonstrated high turf performance, with an excellent record of persistence and spread under adverse conditions. The variety also has exhibited very good rhizome and tiller development under turf maintenance.

What is claimed is:

1. A new and distinct variety of Kentucky bluegrass plant, substantially as herein shown and described, characterized particularly by a rich, dark green color, excellent resistance to strip smut disease, moderately small particles and spikelets, and moderately fine leaf texture.

No references cited.

ROBERT E. BAGWILL, Primary Examiner